United States Patent
Colwell et al.

US006752982B2

(10) Patent No.: US 6,752,982 B2
(45) Date of Patent: Jun. 22, 2004

(54) PERSONAL CARE PRODUCT

(75) Inventors: Dennis James Colwell, Mansfield, MA (US); David L. Elliott, North Attleboro, MA (US); Michael J. Moloney, Brimfield, MA (US); Sonia M. Rubico-Jamir, Andover, MA (US); Ron Grosz, Andover, MA (US)

(73) Assignee: The Gillette Company, Boston, MA (US)

(*) Notice: Subject to any disclaimer, the term of this patent is extended or adjusted under 35 U.S.C. 154(b) by 30 days.

(21) Appl. No.: 10/237,491

(22) Filed: Sep. 9, 2002

(65) Prior Publication Data

US 2003/0232025 A1 Dec. 18, 2003

Related U.S. Application Data

(63) Continuation of application No. 10/167,907, filed on Jun. 12, 2002, now abandoned.

(51) Int. Cl.[7] .............................. A61K 7/32; A61K 7/00
(52) U.S. Cl. ......................... 424/65; 424/400; 424/407
(58) Field of Search .............................. 424/65; 401/175, 401/176, 68, 82, 83, 84

(56) References Cited

U.S. PATENT DOCUMENTS

| | | |
|---|---|---|
| D27,864 S | 11/1897 | Blackman |
| 692,481 A | 2/1902 | Robinson |
| 964,422 A | 7/1910 | Hood |
| 1,669,016 A | 5/1928 | O'Neil |
| 1,791,359 A | 2/1931 | Henriksen |
| 2,101,540 A | 12/1937 | Gullich |
| 2,165,420 A | 7/1939 | Siefert |
| 2,174,779 A | 10/1939 | Delorme |
| 2,613,185 A | 10/1952 | Marshall |
| 2,980,083 A | 1/1961 | Bell |
| D201,229 S | 5/1965 | Burke |
| 3,294,692 A | 12/1966 | Kelly et al. |
| 3,479,429 A | 11/1969 | Morshauser et al. |
| 3,769,225 A | 10/1973 | Matthaei |
| 3,832,431 A | 8/1974 | Matthaei |
| 4,120,948 A | 10/1978 | Shelton |
| 4,202,879 A | 5/1980 | Shelton |
| 4,393,643 A | 7/1983 | Fryar et al. |
| 4,511,552 A | 4/1985 | Cox |
| 4,524,062 A | 6/1985 | Laba et al. |
| 4,578,207 A | 3/1986 | Holdt et al. |
| 4,714,085 A | 12/1987 | Von Kleinsorgen |
| 4,743,443 A | 5/1988 | Pisani et al. |
| 4,786,449 A | 11/1988 | Smit |
| 4,879,063 A | 11/1989 | Wood-Rethwill et al. |
| 5,217,639 A | 6/1993 | Mottola |
| D344,154 S | 2/1994 | Mottola |
| 5,330,751 A | 7/1994 | Curtin et al. |
| 5,417,964 A | 5/1995 | Carlson, Sr. et al. |
| 5,538,161 A | 7/1996 | Koehler et al. |
| 5,587,153 A | 12/1996 | Angelone, Jr. et al. |
| 5,705,171 A | 1/1998 | Iovanni et al. |
| 5,759,974 A | 6/1998 | Menke et al. |
| 5,965,501 A | 10/1999 | Rattinger |
| D423,713 S | 4/2000 | Szekely |
| D430,346 S | 8/2000 | van der Hagen |
| 6,096,296 A | 8/2000 | Alflen et al. |
| D443,951 S | 6/2001 | Look |
| D444,264 S | 6/2001 | Look |
| D444,265 S | 6/2001 | Look |
| D444,593 S | 7/2001 | Look |
| D444,913 S | 7/2001 | Look |
| D446,356 S | 8/2001 | Look |
| D446,606 S | 8/2001 | Look |
| D446,607 S | 8/2001 | Look |
| D450,882 S | 11/2001 | Colwell et al. |
| D454,227 S | 3/2002 | Look |
| D454,228 S | 3/2002 | Look |
| D454,229 S | 3/2002 | Look |
| D454,414 S | 3/2002 | Look |
| D454,661 S | 3/2002 | Look |
| D454,662 S | 3/2002 | Look |
| D454,663 S | 3/2002 | Look |
| D454,664 S | 3/2002 | Look |
| D454,665 S | 3/2002 | Look |
| D454,666 S | 3/2002 | Look |
| D454,983 S | 3/2002 | Look |
| D454,984 S | 3/2002 | Look |
| D454,985 S | 3/2002 | Look |
| 6,506,369 B2 * | 1/2003 | Ambler et al. ................ 424/65 |
| 2002/0041788 A1 | 4/2002 | Look et al. |

FOREIGN PATENT DOCUMENTS

| | | |
|---|---|---|
| DE | 199 21 183 A1 | 9/2000 |
| EP | 0 116 406 | 8/1984 |
| FR | 977194 | 3/1951 |
| GB | 1013559 | 12/1965 |
| GB | 2014507 A | 8/1979 |
| GB | D2081820 | 7/1999 |
| WO | WO 99/23998 | 5/1999 |
| WO | WO 00/19861 | 4/2000 |
| WO | WO 01/91605 | 12/2001 |

OTHER PUBLICATIONS

The Body Shop Skin & Hair Care•Products catalog holiday edition c 1995; p. 16 makeup indicated by arrows.
"Bac deo–stick", undated, prior to Jun. 12, 2002.
"Bac deo–stick" undated, prior to Jun. 12, 2002.

\* cited by examiner

*Primary Examiner*—Shelley A. Dodson
(74) *Attorney, Agent, or Firm*—Fish & Richardson P.C.

(57) ABSTRACT

An antiperspirant or deodorant composition has a marbled appearance.

30 Claims, 2 Drawing Sheets

PERSONAL CARE PRODUCT

This application is a continuation (and claims the benefit of priority under 35 U.S.C. §120) of U.S. application Ser. No. 10/167,907, filed Jun. 12, 2002 now abandoned.

TECHNICAL FIELD

This invention relates to methods of manufacturing personal care products.

BACKGROUND

Antiperspirant and deodorant compositions are well known personal care products. The compositions come in a variety of forms and may be formulated, for example, into aerosols, pumps, sprays, liquids, roll-on, lotion, creams, and sticks (both hard and soft), etc.

There are various types of stick antiperspirant compositions. In one type, an antiperspirant salt is suspended in an anhydrous vehicle often including a solid water-insoluble wax. In a second type, an antiperspirant salt is dissolved in a liquid vehicle such as propylene glycol and gelled with a gelling agent such as dibenzylidene sorbitol. A third type includes an emulsion of an aqueous phase containing the antiperspirant salt and an oil phase containing, for example, a volatile silicone, fragrances, gellants, and other additives.

SUMMARY

Generally, the invention relates to an antiperspirant or deodorant composition having a marbled appearance. "Marbled appearance", as used herein, refers to a product having an application surface that is irregularly colored with mottling or streaking. The marbled appearance is preferably two colors, one being white and the other non-white, although colors other than white and patterns having more than two colors are possible.

In one aspect, the invention features a composition having a marbled appearance that includes two portions. The first portion has a first color and includes an antiperspirant salt or deodorant active. The second portion has a second color and also includes an antiperspirant salt or deodorant active.

In another aspect, the invention features a composition having a marbled appearance that again includes two portions. The first portion has a first color and includes an antiperspirant salt or deodorant active. The second portion has a second color. One or both portions has a melt viscosity of at least 1200 cp at 65° C., preferably between 1500 cp and 5000 cp at 65°, and more preferably between 2000 cp and 4000 cp at 65°. Melt viscosity is measured 3° C. above the melting point of the formulation at a shear rate of 1 sec$^{-1}$ using a TA Instruments AR-1000 rheometer. The relatively high viscosity of one or both portions can provide reduced mixing of the two portions during manufacture. This controlled rate and degree of mixing achieves the marbled appearance.

In one embodiment, the first portion comprises a volatile silicone, a high melting wax, and from 6 USP weight percent to 25 USP weight percent antiperspirant salt, and the second portion includes a volatile silicone, a high melting wax, and from 6 USP weight percent to 25% weight percent antiperspirant salt.

In another aspect the invention features a method of manufacturing an antiperspirant or deodorant product including a composition with the marbled appearance. The method includes (1) combining a first composition portion having a first color and including an antiperspirant salt with a second color and also including an antiperspirant salt or deodorant active, and (2) filling a container with the first composition portion and the second composition portion. Preferably the first and second composition portions are combined before filling the container, although alternatively combining and filling can be done as one step.

In another aspect, the invention features a method of manufacturing an antiperspirant or deodorant product including a composition having a marbled appearance. The method includes (1) combining a first composition portion having a first color and including an antiperspirant salt with a second composition portion having a second color, and (2) filling a container with the first composition portion and the second composition portion. The first composition portion and/or the second composition portion has a melt viscosity of at least 1200 cp at 65° C. Preferably the first and second composition portions are combined before filling the container, although alternatively the combining and filling can be done as one step.

In a further aspect, the invention again features a method of manufacturing an antiperspirant or deodorant product including a composition having a marbled appearance. The method includes (1) combining a first composition portion having a first color and including an antiperspirant salt with a second composition portion having a second color under predominantly laminar flow conditions and (2) filling a container with the combined first composition portion and second composition portion. "Predominantly laminar" as used herein, means filling conditions with Reynolds Number for flow that is in the transition region between laminar and turbulent flow or lower for a particular formulation. The transition from laminar to turbulent flow generally occurs at a Reynolds Number between 2000 and 4000. Thus, "predominantly laminar" conditions occur at a Reynolds Number below about 4000, and preferably, below a Reynolds Number of about 2000. Predominantly laminar conditions result in minimal fluid turbulence, thereby reducing mixing of the two fluid portions. The result is that the fluid portions, only partially mixed, can be cooled below their melt points, resulting in the marbled appearance.

Other features and advantages of the invention will be apparent from the description of an embodiment thereof, the drawings, and from the claims.

DETAILED DESCRIPTION

Figure 1:
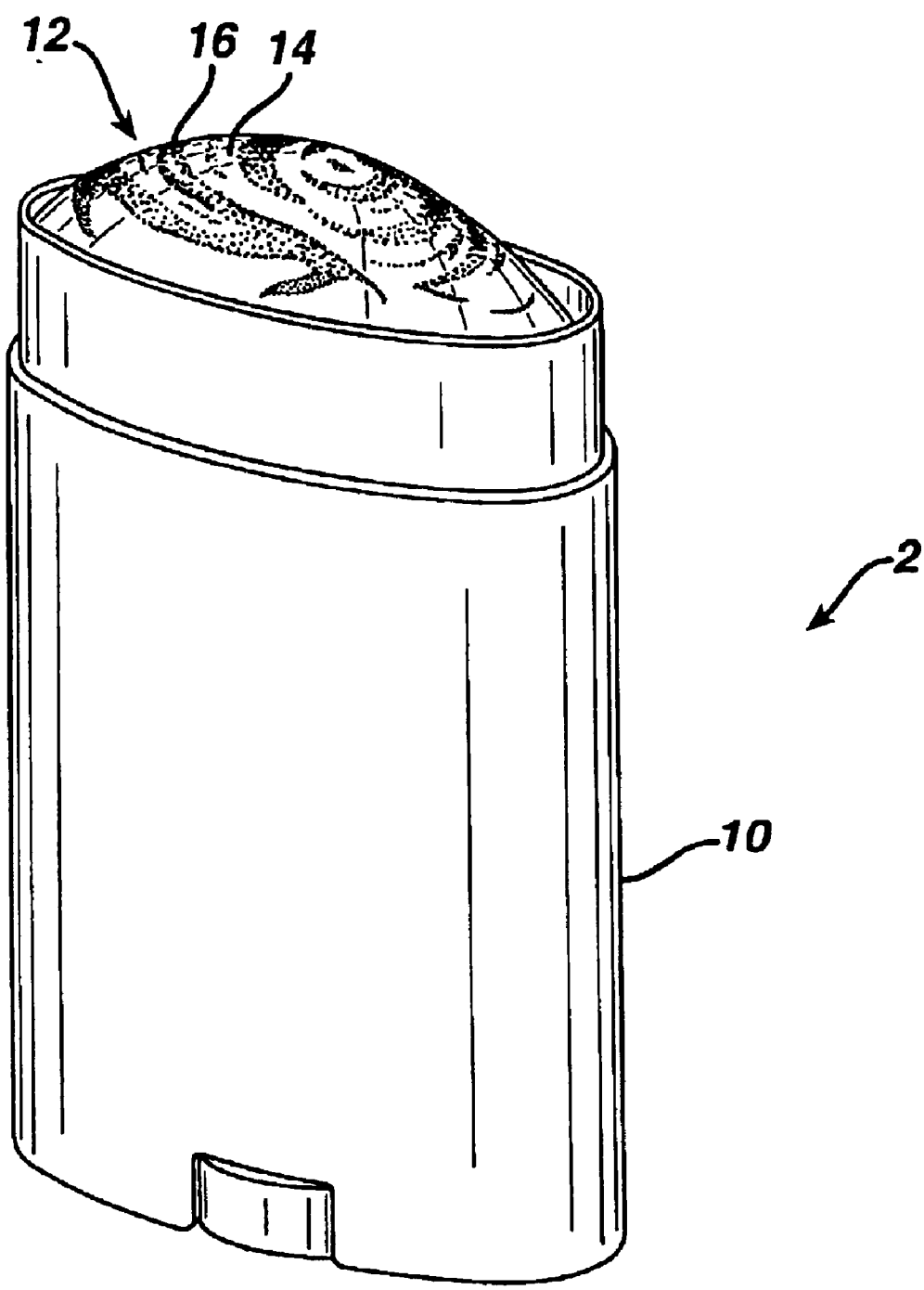
FIG. 1. is a perspective view of an antiperspirant product including a composition having a marbled appearance.

Referring to FIG. 1, antiperspirant product 2 includes a container 10 and an antiperspirant composition 12 having a marbled appearance. The antiperspirant composition includes a white first portion 14 and a blue second portion 16. The portions may be partially mixed at their interfaces, but "first portion" and "second portion", as used herein, means the first portion or the second portion prior to the mixing. Of course, product 10 alternatively can also include a third portion, a fourth portion, etc., each having a different composition and color.

One or both of the portions in the antiperspirant product may include an antiperspirant salt suspended in an anhydrous, hydrophobic vehicle including a volatile silicone and/or a high melting component such as a wax.

The preferred antiperspirant salts are aluminum salts and aluminum zirconium salts. Preferred aluminum salts are those having the general formula $Al_2(OH)_{6-a}X_a$ wherein X is Cl, Br, I, or $NO_3$, and a is about 0.3 to about 5, preferably about 0.8 to about 2.5, more preferably about 1 to about 2 (such that the Al to X mole ratio is about 0.9:1 to about 2.1:1). These salts generally have some water of hydration associated with them, typically on the order of 1 to 6 moles per mole of salt. Most preferably, the aluminum salt is aluminum chlorohydrate (i.e., X is Cl in the above formula), especially ⅚ basic aluminum chlorohydrate where a is about 1, such that the aluminum to chlorine mole ratio is about 1.9:1 to 2.1:1. Aluminum chlorohydrate is referred to as "ACH" herein.

Preferred aluminum-zirconium salts are mixtures or complexes of the above-described aluminum salts with zirconium salts of the formula $ZrO(OH)_{4-pb}Y_b$ wherein Y is Cl, Br, I, $NO_3$, or $SO_4$, b is about 0.8 to 4, and p is the valence of Y. The zirconium salts also generally have some water of hydration associated with them, typically on the order of 1 to 7 moles per mole of salt. Preferably the zirconium salt is zirconium hydroxychloride of the formula $ZrO(OH)_{4-b}Cl_b$ wherein b is about 0.8 to 4, preferably about 1.0 to about 4. The aluminum-zirconium salts encompassed by the present invention have an Al:Zr mole ratio of about 2 to about 10, and a metal:X+Y ratio of about 0.73 to about 2.1, preferably about 0.9 to 1.5. A preferred salt is aluminum-zirconium chlorohydrate (i.e. X and Y are Cl), which has an Al:Zr ratio of about 2 to about 10 and a metal:Cl ratio of about 0.9 to about 2.1. Thus, the term aluminum-zirconium chlorohydrate is intended to include the tri-, tetra-, penta- and octa-chlorohydrate forms. Aluminum-zirconium chlorohydrate is referred to as "AZCH" herein. Generally, the aluminum-zirconium antiperspirant salts also contain a neutral amino acid such as glycine, typically in an amount to provide a Zr:Gly ratio of about 1:1 to 4:1.

The preferred ACH and AZCH salts are of the enhanced efficacy type. By "enhanced efficacy salt" is meant an antiperspirant salt which, when reconstituted as a 10% aqueous solution, produces an HPLC chromatogram (as described, for example, in U.S. Pat. No. 5,330,751, which is incorporated herein by reference) wherein at least 50%, preferably at least 70%, most preferably at least 80%, of the aluminum is contained in two successive peaks, conveniently labeled peaks 3 and 4, and wherein the ratio of the area under peak 4 to the area under peak 3 is at least 0.5, preferably at least 0.7, and more preferably at least 0.9 or higher. Particularly preferred, for example, are salts wherein at least 30%, more preferably at least 40%, of the aluminum is contained in peak 4. The aluminum present in peaks 3 and 4 should be of the $Al^c$ type, not $Al^b$, when analyzed by the ferron test. Enhanced efficacy aluminum chlorohydrate is referred to as "ACH'" herein. Enhanced efficacy aluminum-zirconium chlorohydrate is referred to as "AZCH'" herein.

HPLC analysis means that chromatograms were obtained as follows: Salt solutions are evaluated for aluminum polymer distribution by HPLC at a concentration of about 10% Al or Al—Zr salt. If the solution to be analyzed is at a higher salt concentration, it is diluted with sufficient water to bring the salt concentration to about 10%. A 1.0 µL sample is pumped through a 4.6 mm×500 mm column packed with Nucleosil 100-5 silica (Keystone Scientific Inc.) using a 0.01M aqueous nitric acid solution as the eluent. The flow rate of the mobile phase was controlled at 0.5 mL/min with an LDC/Milton Roy ConstaMetric-II metering pump (ThermoQuest Inc). HPLC profiles were recorded and processed which has a computerized system that included the Millennium 32 Chromatography Manager software from the Waters Corp. A Waters 2410 differential refractometer was used as the refractive index detector. The HPLC profiles are read from left to right (higher to lower molecular weight). Following this technique, peak 3 typically appears at a retention time of 11.05–11.26 minutes (kd~0.58–0.62) and peak 4 typically appears at a retention time of 11.91–12.16 minutes (kd~0.69–0.73). Naturally, of course, other HPLC techniques which use different column materials, eluents and flow rates can be used provided that they sufficiently resolve peaks 3 and 4 with an acceptable degree of precision (i.e. the technique must be capable of resolving the Al into as least four distinct peaks). Obviously, such other techniques may place peaks 3 and 4 at different retention times from those given above.

An alternative enhanced efficacy antiperspirant salt are those described in U.S. Ser. No. 09/696,271, filed on Oct. 25, 2000, which has been assigned to the same assignee as the present application and is hereby incorporated by reference. Examples of these salts are aluminum-zirconium tetrachlochlorohydrate or aluminum-zirconium octochlorohydrate with an HPLC peak 5 area content of at least 45%. These enhanced efficacy salts will be referred to as "$E^5AZCH$'" herein.

In this application, weight percent (USP) of antiperspirant salt is calculated as anhydrous weight percent in accordance with the U.S.P. method. This calculation excludes any bound water and glycine. For aluminum chlorohydrate and aluminum-zirconium chlorohydrate, the calculation is as follows:

%ACH=%Al[26.98x+17.01(3x−1)+35.45]/26.98x where x=Al/Cl ratio;

%AZCH=%Al{26.98y+92.97+17.01[3y+4−(y+1)/z]+35.45(y+1)/z}/126.98y where y=Al/Zr ratio and z=metal/Cl ratio.

For reference purposes, calculation of antiperspirant salt weight percent in accordance with the U.S.P. method compares to the previously used standard industry method is as follows: 50% ACH (std.)=40.8% (USP); 50% AZCH (std)= 38.5% USP.

A portion or both portions of the antiperspirant composition includes the antiperspirant salt in a perspiration reducing effective amount (typically at a concentration of about 3% to about 25% USP active, more typically about 6% to about 25% USP active).

The anhydrous, hydrophobic vehicle comprises about 60% to 95%, preferably about 70% to 90%, of a portion or the portions of the antiperspirant composition. The vehicle generally includes one or more high melting components that melt at 70° C. or higher and/or a volatile silicone.

The high melting components may include any material suitable for use in an antiperspirant stick which melts at a temperature of about 70° C. or higher. Typical of such materials are the high melting point waxes. These include beeswax, spermaceti, carnauba, bayberry, candelilla, montan, ozokerite, ceresin, and paraffin waxes, semimicrocrystalline and microcrystalline waxes, hydrogenated jojoba oil, and hydrogenated castor oil (castor wax). The preferred wax is hydrogenated castor oil. Other suitable high melting components include various types of high melting gelling agents such as polyethylene-vinyl acetate copolymers, polyethylene homopolymers, 12-hydroxystearic acid, and substituted and unsubstituted dibenzylidene alditols. Polyethylene homopolymers are described in, for example, U.S. Pat. No. 6,375,938, which is incorporated by reference herein. Typically, the high melting components comprise about 1 to 25%, preferably about 2 to 15%, of the composition.

Volatile silicones include the cyclic polydimethylsiloxanes, also known as cyclomethicones, which have from about 3 to about 6 silicon atoms, and the linear polydimethylsiloxanes, also known as dimethicones, which have from about 2 to about 9 silicon atoms. The linear volatile silicones generally have viscosities of less than about 5 centistokes at 25° C. while the cyclic volatile silicones have viscosities under 10 centistokes; an example is DC 200, which is available from Dow Corning Corp. "Volatile" means that the material has a measurable vapor pressure at room temperature. Cyclomethicones include DC 245, DC 344, and DC 345, all of which are also available from Dow Corning Corporation. Volatile silicones are described further in U.S. Ser. No. 09/672,350, filed Sep. 28, 2000, which is assigned to the same assignee as the present application and is hereby incorporated by reference.

Other components may include, for example, non-volatile silicones, polyhydric alcohols having 3–6 carbon atoms and 2–6 hydroxy groups, fatty alcohols having from 12 to 24 carbon atoms, fatty alcohol esters, fatty acid esters, fatty amides, non-volatile paraffinic hydrocarbons, polyethylene glycols, polypropylene glycols, polyethylene and/or polypropylene glycol ethers of C4–20 alcohols, polyethylene and/or polypropylene glycol esters of fatty acids, and mixtures thereof. The term "fatty" is intended to include hydrocarbon chains of about 8 to 30 carbon atoms, preferably about 12 to 18 carbon atoms.

Non-volatile silicones include polyalkylsiloxanes, polyalkylaryl siloxanes, and polyethersiloxanes with viscosities of about 5 to about 100,000 centistokes at 25° C., polymethylphenylsiloxanes with viscosities of about 15 to about 65 centistokes, and polyoxyalkylene ether dimethylsiloxane copolymers with viscosities of about 1200 to about 1500 centistokes.

Useful polyhydric alcohols include propylene glycol, butylenes glycol, dipropylene glycol and hexylene glycol. Fatty alcohols include stearyl alcohol, cetyl alcohol, myristyl alcohol, oleyl alcohol, and lauryl alcohol. Fatty alcohol esters include $C_{12–15}$ alcohols benzoate, myristyl lactate, cetyl acetate, and myristyl octanoate. Fatty acid esters include isopropyl palmitate, myristyl myristate, and glyceryl monostearate. Fatty amides include stearamide MEA, stearamide MEA-stearate, lauramide DEA, and myristamide MIPA.

Non-volatile paraffinic hydrocarbons include mineral oils and branched chain hydrocarbons with about 16 to 68, preferably about 20 to 40, carbon atoms. An example is hydrogenated polyisobutene with about 24 carbon atoms. Suitable polyethylene glycols and polypropylene glycols will typically have molecular weights of about 500 to 6000, such as PEG-10, PEG-40, PEG-150 and PPG-20, often added as rheology modifiers to alter product appearance or sensory attributes.

Polyethylene and/or polypropylene glycol ethers or $C_{4–20}$ alcohols include PPG-10 Butanediol, PPG-14 Butyl Ether, PPG-5-Buteth-7, PPG-3-Isostearth-9, PPG-3-Myreth-3, Oleth-10, and Steareth-20. Polyethylene and/or polypropylene glycol esters of fatty acids include PEG-8 Distearate, PEG-10 Dioleate, and PPG-26 Oleate. These are generally added to give emollient properties.

The above list of materials is by way of example only and is not intended to be a comprehensive list of all potential antiperspirant stick components. Other low melting waxes, non-volatile emollients and suitable components are readily identifiable to those skilled in the art. Of course, other ingredients such as colloidal silicas, particulate polyolefins, talcum materials, fragrances, colorants and preservatives may also be included as desired. For example, the composition may include up to about 10% fragrance or about 2% colorant by weight.

Deodorant active ingredients may also be included as desired. A suitable deodorant active is any agent that inhibits, suppresses, masks or neutralizes malodor. These may include (1) antimicrobial or bactericidal agents which kill the bacteria responsible for malodor production, (2) agents which inhibit or suppress or interfere with the bacterial enzymatic pathway that produces malodor, and (3) agents which mask or absorb or neutralize malodor. Fragrances are not considered deodorant active ingredients within the meaning of this application. Examples of deodorant actives include triclosan, triclocarban, usnic acid salts, zinc phenolsulfonate, b-chloro-D-alanine, D-cycloserine, aminooxyacetic acid, cyclodextrin, sodium bicarbonate. The composition generally may comprise, by weight, about 0.01% to about 10%, preferably about 0.1% to about 6%, deodorant active.

EXAMPLE

An antiperspirant composition having a marbled appearance included two portions (one blue, one white) having the following formulas:

| White Portion | |
|---|---|
| INGREDIENTS | % WEIGHT |
| PPG-14 Butyl Ether | 11.00 |
| Crodamol MM[1] | 1.92 |
| Castor Wax[2] | 5.00 |
| Stearyl Alcohol | 18.34 |
| Performalene 655[3] | 2 |
| Heat to 95° C. and hold 10 minutes | |
| Cool to 70 C. (69–75° C.) | |
| PREMIX | 58.89 |
| Fragrance[4] | 0.85 |
| Encapsulated Fragrance[5] | 2 |
| Pour at 49–53° C. | |
| | 100.00 |
| PREMIX | |
| Volatile Silicone (D5)[6] | 35.490 |
| AZCH" Powder | 22.500[7] |
| Silica (Aerosil R972)[8] | 0.720 |
| Silica (Aerosil 300)[9] | 0.180 |
| Total | 58.890 |

[1]Myristyl myristate emollient (Croda).
[2]MP70 Castor Wax, a modified castor oil purchased from CasChem.
[3]Polyethylene homopolymer from New Phase Technology.
[4]Fragrance purchased from [IFF].
[5]Encapsulated fragrance purchased from Haarmann and Reimer.
[6]Purchased from Dow Corning (Dow Corning Fluid 245).
[7]USP wt % = 16.4–17.1%.
[8]Purchased from Degussa Corp.
[9]Purchased from Degussa Corp.

| Blue Portion | |
|---|---|
| INGREDIENTS | % WEIGHT |
| PPG-14 Butyl Ether | 11.00 |
| Crodamol MM | 1.92 |

-continued

Blue Portion

| INGREDIENTS | % WEIGHT |
|---|---|
| Castor Wax | 5.00 |
| Stearyl Alcohol | 18.14 |
| Performalene 655 | 2 |
| Heat to 95° C. and hold 10 minutes | |
| Cool to 70° C. (69–75° C.) | |
| PREMIX | 58.89 |
| Fragrance 1571 | 0.85 |
| Colorona Dark Blue[1] | 0.20 |
| Encapsulated Fragrance | 2 |
| | 100.00 |
| Pour at 49–53° C. | |
| PREMIX | |
| Volatile Silicone (D5) | 35.490 |
| AZCH" | 22.500 |
| SILICA (R972) | 0.720 |
| SILICA (300) | 0.180 |
| Total | 58.890 |

[1]Pigment/colorant, purchased from Rona, a division of EM Chemicals.

The white portion and the blue portion are prepared as follows.

The white portion is prepared by mixing the components of the premix (the volatile 5 silicone, the AZCH", and the two silicas) followed by a homogenization step. The stearyl alcohol, the castor wax, the Crodamol MM (myristyl myristate), and the PPG-14 butyl ether are heated to about 95° C. to form a molten homogeneous mix. The molten mix is cooled to about 74° C. The premix is then added to the mix while holding the temperature at between 68° C. and 62° C. The mix is then cooled to about 62° C., and the fragrance is added. The completed formulation is then cooled to about 52° C. and then combined with the blue portion (described below).

The blue portion is prepared similarly to the white portion. To the molten stearyl alcohol, castor wax, Crodamol MM, and PPG-14 butyl ether is added the homogenized premix of the volatile silicone, the AZCH", and the two silicas, holding the temperature between 68° C. and 74° C. The mix is then cooled to about 62° C., and the free oil fragrance, encapsulated fragrance, and pigment (Colorona Dark Blue) are added. The mix is cooled to about 52° C. and combined with the white portion.

Figure 2:
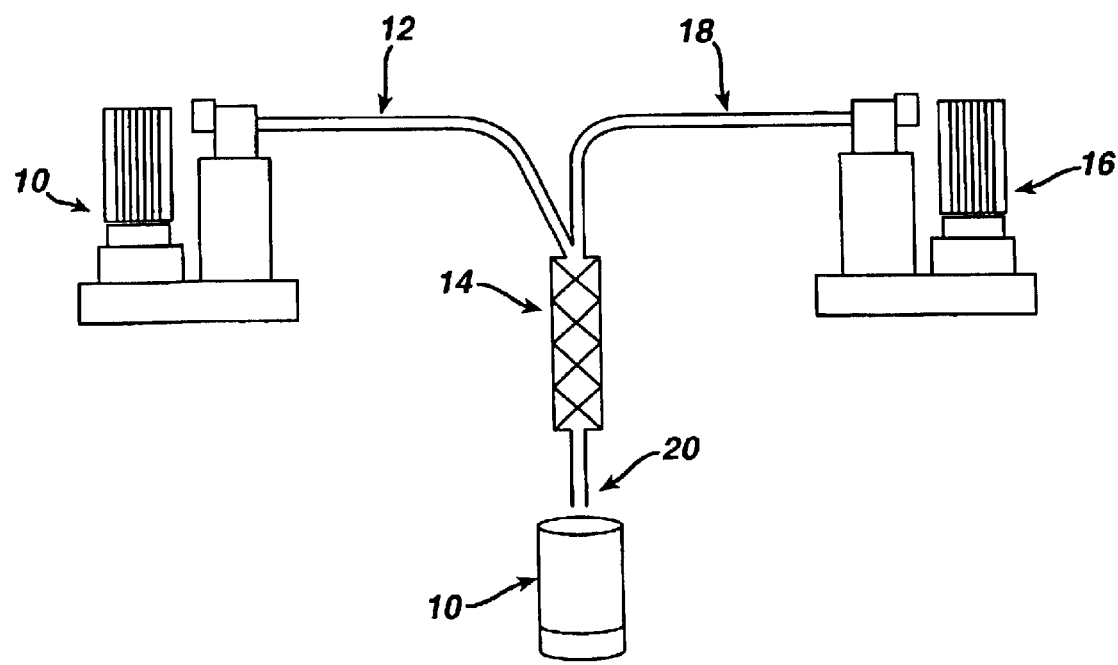
FIG. 2 is a perspective view of a process for manufacturing the antiperspirant product of FIG. 1.

Referring to FIG. 2, the white portion and blue portion are delivered by servomotor driven piston metering pumps 10 and 16, respectively, Hibar model 4S3RV100) into lines 12 and 18. Pumps 10 and 16 are electronically geared to one another to deliver the appropriate quantities of the white and blue portion. The portions preferably are delivered at ratios of white portion:blue portion of from 2:1 to 8:1, for example, 4:1. All product contact surfaces in the process are controlled to maintain the product in a molten state.

The white portion and blue portion are combined in static mixer 14. The static mixer may be, for example, from 2–12 Kenics-type elements available from Chemineer, Inc. or 2–8 Koch SMX-type elements available from Koch-Glitsch, Inc. In the procedure illustrated in FIG. 2, Kenics-type elements having a diameter of 5/8" were used. The number of elements, and the fill rate (discussed below) are selected to maintain a predominantly laminar flow of the two portions and to minimize turbulent zones. The streams of the white portion and the blue portion are introduced parallel or at a low angle into the static mixer. The static mixer reduces smoothly to nozzle tip 20, which has an opening diameter of 0.35 in. Nozzle tip 20 begins the process about 10 mm above the factor seal in container 10 and is retracted during filling to maintain a 10 mm distance above the composition. The fill cycle time can be, for example, from 6 to 10 seconds, resulting in flow rates of from about 380 ml/min to 650 ml/min.

The specific marbled pattern can be varied as desired by adjusting the number of mixing elements, the flow rate through the nozzle, the nozzle diameter, and formulation viscosity.

A number of embodiments of the invention have been described. Nevertheless, it will be understood that various modifications may be made without departing from the spirit and scope of the invention. Accordingly, other embodiments are within the scope of the following claims.

What is claimed is:

1. A product for underarm application, comprising
   a container, and
   a composition, within the container, having an application surface having a marbled appearance, the composition including a first portion having a first color and including an antiperspirant salt and/or a deodorant active, and a second portion having a second color and also including an antiperspirant salt and/or deodorant active.

2. The product of claim 1, wherein the first portion and the second portion each comprises at least 6 USP weight percent of the antiperspirant salt.

3. The product of claim 1, wherein the first portion comprises a volatile silicone, a high melting wax, and from 6 USP weight percent to 25 USP weight percent antiperspirant salt, and the second portion comprises a volatile silicone, a high melting wax, and from 6 USP weight percent to 25% weight percent antiperspirant salt.

4. The product of claim 1, wherein the first portion has a melt viscosity of at least 1200 cp at 65° C.

5. The product of claim 4, wherein the first portion has a melt viscosity of between 1500 cp and 5000 cp at 65°.

6. The product of claim 5, wherein the first portion has a melt viscosity of between 2000 cp and 4000 cp at 65° C.

7. The product of claim 4, wherein the second portion also has a melt viscosity of at least 1200 cp at 65° C.

8. A product for underarm application, comprising
   a container, and
   a composition, within the container, having an application surface having a marbled appearance, the composition including a first portion having a first color and including an antiperspirant salt and/or deodorant active, and a second portion having a second color,
   wherein said first portion and/or said second portion has a melt viscosity of at least 1200 cp at 65° C.

9. The product of claim 8, wherein the first portion and the second portion each comprises at least 6 USP weight percent of the antiperspirant salt.

10. The product of claim 8, wherein the first portion comprises a volatile silicone, a high melting wax, and from 6 USP weight percent to 25 USP weight percent antiperspirant salt, and the second portion comprises a volatile silicone, a high melting wax, and from 6 USP weight percent to 25% weight percent antiperspirant salt.

11. The product of claim 8, wherein said first portion and second portion each has a melt viscosity of at least 1200 cp at 65° C.

12. The product of claim 11, wherein said first portion and said second portion each has a melt viscosity of between 1500 and 5000 cp at 65° C.

13. The product of claim 12, wherein said first portion and said second portion each has a melt viscosity of between 2000 cp and 4000 cp at 65° C.

14. The product of claim 8, wherein said first portion and/or said second portion has a melt viscosity of between 1500 cp and 5000 cp at 65° C.

15. The product of claim 14, wherein said first portion and/or said second portion has a melt viscosity of between 2000 cp and 4000 cp at 65° C.

16. A method of manufacturing an antiperspirant or deodorant product comprising a composition having a marbled appearance within a container, the method comprising combining a first composition portion having a first color and including an antiperspirant salt or a deodorant active with a second composition portion having a second color and also including an antiperspirant salt or deodorant active; and filling the container with the first composition portion and the second composition portion to provide the composition having the marbled appearance.

17. The method of claim 16, wherein the first composition portion and the second composition portion are combined prior to filling the container.

18. The method of claim 16, wherein the first composition portion and second composition portion are combined as the container is filled.

19. The method of claim 16, wherein the first composition portion has a melt viscosity of at least 1200 cp at 65° C.

20. A method of manufacturing an antiperspirant or deodorant product comprising a composition having a marbled appearance within a container, the method comprising combining a first composition portion having a first color and including an antiperspirant salt or a deodorant active with a second composition portion having a second color; and filling the container with the combined first composition portion and second composition portion to provide the composition having the marbled appearance.

21. The method of claim 20, wherein the first composition portion and/or the second composition portion has a melt viscosity of at least 1200 cp at 65° C.

22. The method of claim 20, wherein the first composition portion and second composition portion have a melt viscosity of at least 1200 cp at 65° C.

23. The method of claim 20, wherein the first composition portion has a melt viscosity of at least 1200 cp at 65° C.

24. A method of manufacturing an antiperspirant or deodorant product comprising a composition having a marbled appearance within a container, the method comprising combining, under predominantly laminar flow conditions, a first composition portion having a first color and including an antiperspirant salt or a deodorant active with a second composition portion having a second color; and filling the container with the combined first composition and the second composition portion to provide the composition having the marbled appearance.

25. The method of claim 24, wherein the first composition portion and the second composition portion are combined in a static mixer.

26. The method of claim 24, wherein the second portion also includes an antiperspirant salt or deodorant active.

27. The method of claim 26, wherein the first portion and the second portion each comprises at least 6 USP weight percent of the antiperspirant salt.

28. The method of claim 24, wherein the first composition portion comprises a volatile silicone, a high melting wax, and from 6 USP weight percent to 25 USP weight percent antiperspirant salt, and the second composition portion comprises a volatile silicone, a high melting wax, and from 6 USP weight percent to 25% weight percent antiperspirant salt.

29. The method of claim 24, wherein the first composition portion and/or the second composition portion has a melt viscosity of at least 1200 cp at 65° C.

30. The method of claim 24, wherein the first composition portion and the second composition portion have melt viscosities of between 1500 cp and 5000 cp at 65° C.

* * * * *

UNITED STATES PATENT AND TRADEMARK OFFICE
CERTIFICATE OF CORRECTION

PATENT NO. : 6,752,982 B2
DATED : June 22, 2004
INVENTOR(S) : Dennis James Colwell et al.

It is certified that error appears in the above-identified patent and that said Letters Patent is hereby corrected as shown below:

Tilte page,
Item [56], References Cited, FOREIGN PATENT DOCUMENTS,
"DE 199 21 183 A1 9/2000" should read -- DE 199 21 183 A1 11/2000 --.

Signed and Sealed this

Fifth Day of April, 2005

JON W. DUDAS
*Director of the United States Patent and Trademark Office*